United States Patent
Sakamoto et al.

(10) Patent No.: US 9,937,361 B2
(45) Date of Patent: Apr. 10, 2018

(54) PARTICLE BEAM IRRADIATION APPARATUS

(71) Applicant: MITSUBISHI ELECTRIC CORPORATION, Chiyoda-ku, Tokyo (JP)

(72) Inventors: Yusuke Sakamoto, Tokyo (JP); Yuehu Pu, Tokyo (JP); Hisashi Harada, Tokyo (JP); Taizo Honda, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 101 days.

(21) Appl. No.: 15/110,600

(22) PCT Filed: Jan. 10, 2014

(86) PCT No.: PCT/JP2014/050295
§ 371 (c)(1),
(2) Date: Jul. 8, 2016

(87) PCT Pub. No.: WO2015/104828
PCT Pub. Date: Jul. 16, 2015

(65) Prior Publication Data
US 2016/0325116 A1 Nov. 10, 2016

(51) Int. Cl.
*A61N 5/10* (2006.01)

(52) U.S. Cl.
CPC ......... *A61N 5/1043* (2013.01); *A61N 5/1071* (2013.01); *A61N 2005/1087* (2013.01)

(58) Field of Classification Search
CPC ................ A61N 5/1043; A61N 5/1071; A61N 2005/1087
(Continued)

(56) References Cited

U.S. PATENT DOCUMENTS

2004/0227104 A1 11/2004 Matsuda et al.
2007/0259511 A1* 11/2007 Murrell ................. H01J 37/304
438/535

(Continued)

FOREIGN PATENT DOCUMENTS

EP      2 392 383 A1     12/2011
JP      2004-358237 A    12/2004
(Continued)

OTHER PUBLICATIONS

International Search Report (PCT/ISA/210) dated Feb. 4, 2014, by the Japanese Patent Office as the International Searching Authority for International Application No. PCT/JP2014/050295.

(Continued)

*Primary Examiner* — Nicole Ippolito
(74) *Attorney, Agent, or Firm* — Buchanan Ingersoll & Rooney PC

(57) ABSTRACT

In a particle beam irradiation apparatus that controls a scanning apparatus so that each irradiation position is irradiated with a particle beam a rescan-count number of times by repeating for the rescan-count number of times the irradiation of all irradiation positions in the irradiation target, the irradiation apparatus includes a calculator that receives either one of a rescan count n or a beam intensity J that is a particle beam dose per unit time, to calculate a maximum value of the other satisfying the following conditional expression (P1) for all irradiation positions to present the maximum value to a user.

$$J^* t_i \leq d_i/n \qquad (P1)$$

3 Claims, 8 Drawing Sheets

(58) Field of Classification Search
USPC ... 250/492.1, 492.2, 492.21, 492.22, 492.23, 250/492.3, 396 R, 397
See application file for complete search history.

(56) References Cited

U.S. PATENT DOCUMENTS

| | | | |
|---|---|---|---|
| 2008/0151247 A1* | 6/2008 | Salnik | G01N 21/1717 356/432 |
| 2010/0243911 A1 | 9/2010 | Fujii et al. | |
| 2011/0297849 A1 | 12/2011 | Bert et al. | |
| 2011/0297850 A1* | 12/2011 | Claereboudt | A61N 5/10 250/492.1 |
| 2012/0187314 A1 | 7/2012 | Bert et al. | |
| 2015/0025846 A1* | 1/2015 | Klein | G03F 7/70633 702/179 |
| 2015/0038766 A1* | 2/2015 | Pu | A61N 5/103 600/1 |
| 2015/0306427 A1* | 10/2015 | Hirasawa | A61N 5/1075 250/363.08 |
| 2016/0199667 A1* | 7/2016 | Flynn | A61N 5/1043 600/1 |

FOREIGN PATENT DOCUMENTS

| | | |
|---|---|---|
| JP | 2008-154627 A | 7/2008 |
| JP | 2009-066106 A | 4/2009 |
| JP | 2010-253250 A | 11/2010 |
| JP | 2013-094313 A | 5/2013 |

OTHER PUBLICATIONS

Extended European Search Report dated Oct. 2, 2017, issued by the European Patent Office in corresponding European Application No. EP 14877990.3-1666 (7 pages).

* cited by examiner

PARTICLE BEAM IRRADIATION APPARATUS

TECHNICAL FIELD

The present invention relates to a particle beam irradiation apparatus used in particle beam therapy systems, for irradiating a diseased portion such as a tumor with a particle beam by a prescribed dose in accordance with the three-dimensional shape of the diseased portion.

BACKGROUND ART

The particle beam therapy is a method of treating a cancer by imparting to a tumor in the body of a patient an irradiation dose of charged particles such as protons or carbon ions accelerated to about several hundred MeV using an apparatus such as an accelerator. In the method, it is important to form a dose distribution that approximates as much as possible to a target dose distribution prescribed for the tumor by a doctor. The target distribution is, in many cases, uniform inside the tumor and as lower as possible outside the tumor than thereinside.

When an object (including a human body) is irradiated with a particle beam accelerated by an accelerator, a three-dimensional dose distribution is generally formed whose characteristic has a maximum dose peak at one point in the object. This maximum dose peak is referred to as "Bragg peak". When a maximum dose peak exists at one point in a three-dimensional space, the peak point is defined as "irradiation position" of the particle beam. In order to form a three-dimensional target dose distribution using a particle beam having the above-described peak structure, some contrivance is needed.

One of methods of forming a target dose distribution is a scanning irradiation method. In order to employ the method, a mechanism such as electromagnets is basically used that arbitrarily deflects the particle beam in two directions, i.e., in the X- and Y-directions perpendicular to the Z-direction, the traveling direction of the particle beam. A function is further needed that arbitrarily varies in the Z-direction the position where the Bragg peak is formed, by adjusting the energy level of the particles. The accelerator, which is a particle beam generating apparatus, is generally provided with a mechanism of adjusting the energy level. A plurality of irradiation positions (also referred to as spots) are set in a tumor, and then each irradiation position is sequentially irradiated with the particle beam using the above two mechanisms. Dose balance to be imparted to each irradiation position is preliminarily adjusted so that summation of individual dose distributions imparted to each irradiation position resultantly forms a target dose distribution.

In general, it takes less than 1 msec to scan-shift the particle beam from an irradiation position to a next irradiation position by deflecting the beam in the X-Y direction, while it takes approximately 100 msec to shift the Bragg peak position in the Z-direction by varying the beam energy level. For that reason, the ordinary sequence of irradiating each irradiation position is such that all irradiation positions corresponding to an energy level of the beam are irradiated first with the beam of the energy level by scanning the particle beam in the X-Y direction, and then the energy level is changed to a next one.

When the Bragg peak position is shifted in the Z-direction by varying the energy level, irradiation with the particle beam must be always stopped, that is, the beam must be interrupted. The scanning irradiation method is classified into the following methods depending on the way of scanning in the X-Y direction.

A scanning irradiation method in which the particle beam is interrupted during scan-shifting from an irradiation position to a next irradiation position is called a spot scanning method or a discrete spot scanning method. For example, in the spot scanning method, a mechanism for measuring a dose imparted to each irradiation position is provided, and the method is implemented in such a way that the particle beam is once interrupted when a measured dose reaches a prescribed dose to be administered to an irradiation position, and then the particle beam is scan-shifted to a next irradiation position.

In a case of no interruption of the particle beam during scan-shifting from an irradiation position to a next irradiation position, a scanning irradiation method is classified into two methods. One is a method in which a mechanism is provided for measuring a dose imparted to each irradiation position, and the particle beam is scan-shifted to a next irradiation position without interrupting the beam at the time when the measured dose reaches to a certain value. This method is referred to as a raster scanning method (see, for example, Patent Document 1). Since the irradiation is continued during scan-shifting of the particle beam, the summation of a distribution of doses imparted during scan-shifting and that of doses imparted not during scan-shifting but during staying at irradiation positions is adjusted to a target dose distribution.

The other is a line scanning method in the case of no interruption of the particle beam during scan-shifting from an irradiation position to a next irradiation position. In this method, the irradiation target is irradiated with the particle beam by continuing scanning of the particle beam without staying at each irradiation position. Functions of keeping constant the beam intensity, which is a dose imparted per unit time, and of varying the scanning speed arbitrarily are provided for scanning the particle beam at a low speed near an irradiation position to which a high dose to be imparted and at a high speed near an irradiation position to which a low dose to be imparted. By controlling the scanning speed in this way to be inverse-proportional to a dose to be administered to each irradiation position, the resultant summation of a dose distribution is adjusted to be a target distribution.

In each scanning method above, although a target dose distribution should be obtained according to calculation, a dose distribution actually obtained may not be a target one since there are various uncertainties in practical irradiation. The uncertainties are caused such as by instability in the position and intensity of the particle beam, a positional error in fastening a patient, error in CT data of the patient, a signal delay in the control equipment, and noise, for example. Due to influence of these uncertainties, an actual dose distribution may differ from calculated one. Moreover, in a case of a tumor particularly in a liver or a respiratory organ such as a lung, it is difficult to impart an irradiation dose to the tumor in accordance with a treatment plan because the position of the tumor, conditions around the tumor and the like are changing temporally owing to respiration of the patient.

There has been a method referred to as "rescanning" or "repainting" for resolving the above problems (see, for example, Patent Document 2). In the method, each irradiation position is dividedly irradiated multiple times with the particle beam. The method is based on the concept that error in a dose distribution is canceled out and reduced by summing the multiple time irradiations. The number of divided irradiation is referred to as a rescan count. The sequence of irradiation is such that the particle beam of an energy level is scanned at first in the X-Y direction to irradiate once all irradiation positions corresponding to the energy level. After that, each irradiation position is irradiated again with the energy level remaining unchanged. The irradiation is repeated for a rescan-count number of times, and then the energy level is changed to a next one. The rescan count may be different for each energy level or may be the same for all energy levels. Generally, influence of the error is cancelled out and reduced more as the rescan count is increased.

PRIOR ART DOCUMENT

Patent Document

Patent Document 1: JP2009-066106 A (paragraph [0014])
Patent Document 2: JP2008-154627 A

SUMMARY OF THE INVENTION

Problem that the Invention is to Solve

The rescanning is applicable to any of the spot scanning method, the raster scanning method, and the line scanning method. In any of the methods, when the rescan count is increased, a single dose to be administered to each irradiation position must be reduced accordingly.

However, in the raster scanning method, since the particle beam is not interrupted during scanning as described above, a non-zero dose is inevitably imparted during scanning even though the stationary time of the beam at an irradiation position is set to be zero. Likewise, in the line scanning method, since the scanning speed of the particle beam has a physical upper limit, a dose to each irradiation position cannot be reduced to zero, i.e., a lower limit exists for the dose even when the scanning is performed at a maximum speed.

In both of the raster scanning method and the line scanning method, a lower limit of the dose depends on the maximum scanning speed, the beam intensity, and a distance between irradiation positions. Increasing the rescan count reduces a single dose to be administered to each irradiation position and may cause the single dose to be lower than the lower limit. Even in that case, a dose comparable to the lower limit is necessarily imparted, resulting in occurrence of an excessive dose higher than a planned value.

Such a problem has not been strongly recognized, and there has been no proposals how to set a proper rescan count.

The present invention is therefore aimed at providing a particle beam irradiation apparatus that allows for setting a proper rescan count in a raster scanning method or a line scanning method.

Means for Solving the Problem

According to the present invention, in a particle beam irradiation apparatus that has a scanning apparatus deflecting a particle beam in a two X-Y directions perpendicular to a traveling direction of the beam, to scan the beam two-dimensionally over irradiation positions in an irradiation target to be irradiate with the particle beam; a memory that stores position information on the irradiation positions, information on a dose to be administered to each irradiation position, and information on scan speed of the scanning apparatus; a controller that controls the scanning apparatus; and a dose monitor that measures a dose of the particle beam, wherein the controller controls the scanning apparatus so that each irradiation position in the irradiation target are irradiated with the particle beam a rescan-count number of times by repeating for the rescan-count number of times the irradiation of all irradiation positions in a two-dimensional X-Y plane by repeating scan-shifting of the particle beam to a next irradiation position without interrupting the irradiation with the particle beam after a dose measured with the dose monitor reaches a dose calculated on the basis of the dose to be administered to a current irradiation position, stored in the memory, the particle beam irradiation apparatus includes a calculator that receives either one of a rescan count n or a beam intensity J that is a dose of the particle beam per unit time, to calculate a maximum value of the other satisfying the following conditional expression (P1) for all irradiation positions to present the maximum value to a user, $$J*t_i \leq d_i/n \tag{P1}$$

where i is an irradiation position number; $t_i$ is a time for the particle beam to be scan-shifted from an irradiation position i−1 to an irradiation position i, calculated from the scan speed information and the position information stored in the memory; and $d_i$ is a dose to be administered to the irradiation position i, stored in the memory.

Furthermore, in a particle beam irradiation apparatus that has a scanning apparatus deflecting a particle beam in a two X-Y directions perpendicular to a traveling direction of the beam, to scan the beam two-dimensionally over irradiation positions in an irradiation target to be irradiate with the particle beam; a memory that stores position information on the irradiation positions, information on a dose to be administered to each irradiation position, and information on scan speed of the scanning apparatus; and a controller that controls the scanning apparatus, wherein the controller controls the scanning apparatus so that each irradiation position in the irradiation target are irradiated with the particle beam a rescan-count number of times by repeating for the rescan-count number of times the irradiation of all irradiation positions in a two-dimensional X-Y plane by repeating scan-shifting of the particle beam from a current irradiation position to a next irradiation position at a speed calculated on the basis of a dose to be administered to each irradiation position, stored in the memory, the particle beam irradiation apparatus includes a calculator that receives either one of a rescan count n or a beam intensity J that is a dose of the particle beam per unit time, to calculate a maximum value of the other satisfying the following conditional expression (P2) for all irradiation positions to present the maximum value to a user, $$J*t_{i,min} \leq d_i/n \tag{P2}$$

where i is an irradiation position number; $t_{i,min}$ is a minimum time for the particle beam to be able to be scan-shifted from an irradiation position i to an irradiation position i+1, calculated from the scan speed information and the position information stored in the memory; and $d_i$, is a dose to be administered to the irradiation position i, stored in the memory.

Advantages of the Invention

According to the present invention, a particle beam irradiation apparatus can be provided that allows for setting a proper rescan count in a raster scanning method and a line scanning method and is thereby capable of performing a high reliability irradiation in a shortest possible time.

EMBODIMENTS FOR CARRYING OUT THE INVENTION

Embodiment 1

Figure 1:
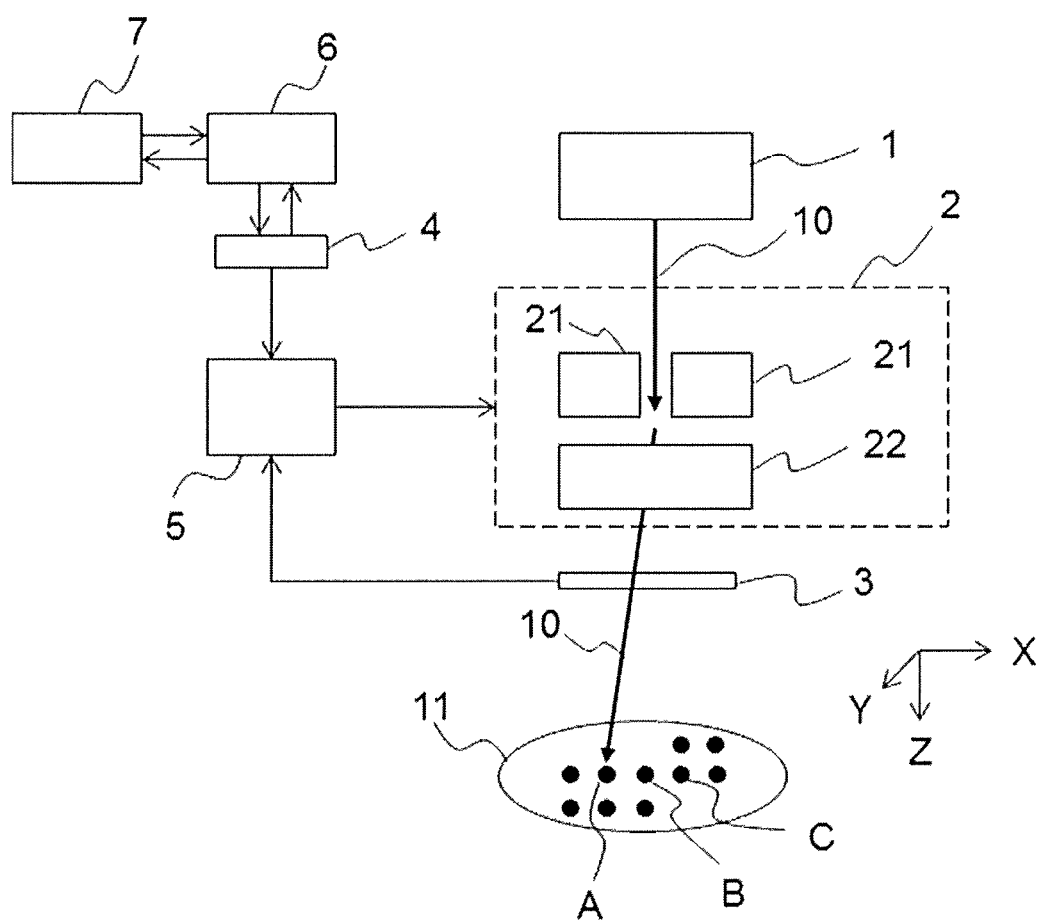
FIG. 1 is a block diagram showing a schematic configuration of a particle beam irradiation apparatus according to Embodiment 1 of the present invention.

FIG. 1 is a block diagram showing a schematic configuration of a particle beam irradiation apparatus according to Embodiment 1 of the present invention. The particle beam irradiation apparatus according to Embodiment 1 includes a particle beam generating apparatus 1 for generating and accelerating particles as a particle beam 10 to a required energy level; and a scanning apparatus 2 for deflecting the particle beam 10 generated by the particle beam generating apparatus 1 in two directions (X- and Y-directions) perpendicular to the traveling direction (Z-direction) of the particle beam, to scan the particle beam over given positions in an irradiation target 11, i.e., a tumor of a patient. The particle beam generating apparatus 1 is ordinarily provided with an accelerator for accelerating the particles and a delivery system for delivering the particle beam 10 from the accelerator to the scanning apparatus 2. The particle beam irradiation apparatus further includes a dose monitor 3 for measuring a dose imparted to each position in the irradiation target 11 from the particle beam 10 scanned by the scanning apparatus 2; a memory 4 for storing position information on each irradiation position, information on a dose to be administered to each irradiation position, information on scan speed of the scanning apparatus 2, and the like; a controller 5 for controlling scanning of the scanning apparatus 2; and a calculator 6 for calculating using the information stored in the memory 4 a rescan count or a beam intensity from a beam intensity or a rescan count input via an input/output unit 7. In addition, the position information to be stored in the memory 4 includes, for example, irradiation position numbers, the X- and Y-coordinates of each irradiation position, current values for energizing the scanning electromagnets in the scanning apparatus 2 to deflect the particle beam to each irradiation position in the X-Y direction, an energy level corresponding to the Z-coordinate of each irradiation position, and the like.

Figure 2:
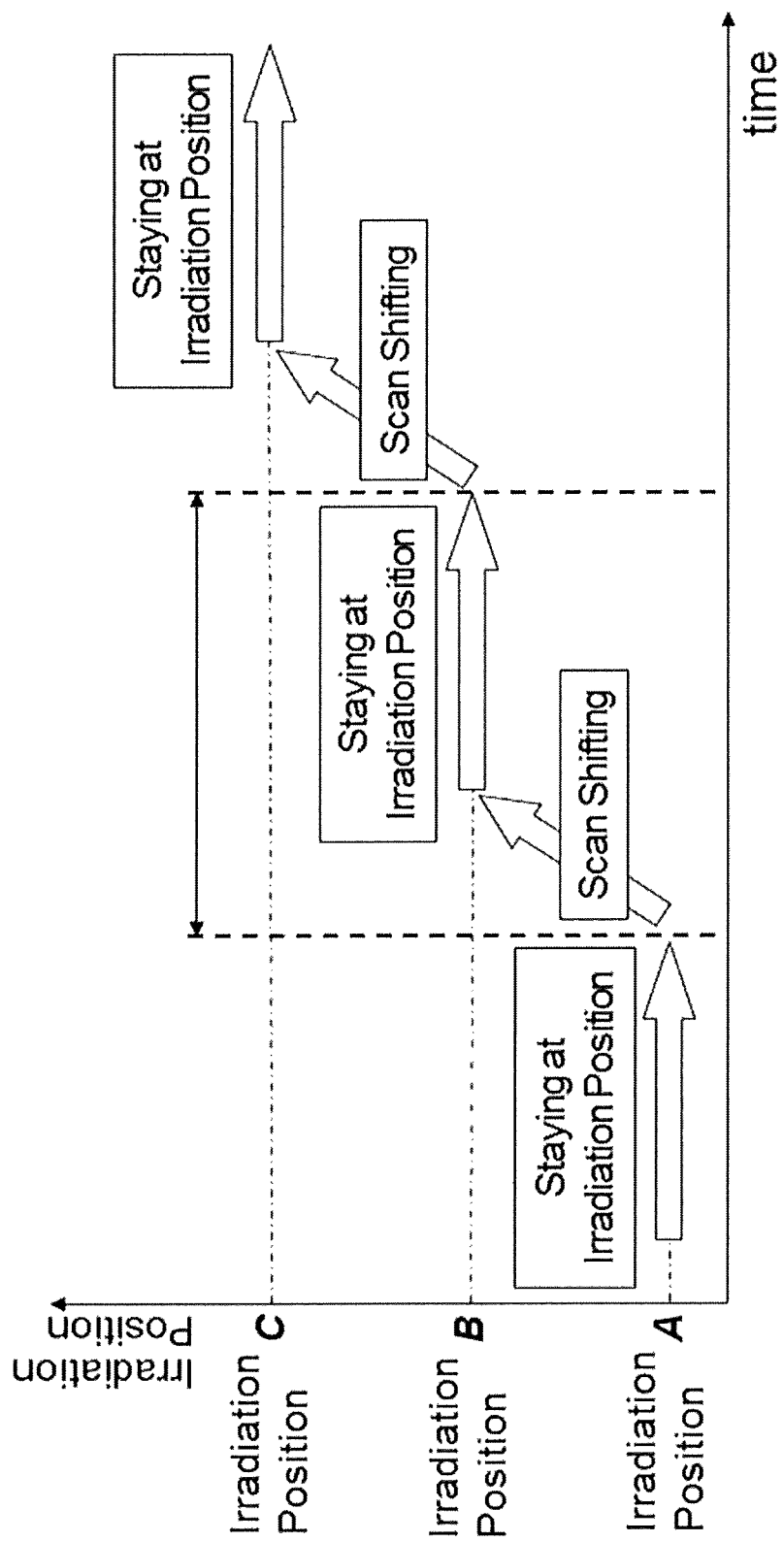
FIG. 2 is a diagram for explaining a basic operation of the particle beam irradiation apparatus according to Embodiment 1 of the present invention.

The particle beam irradiation apparatus according to Embodiment 1 is for implementing a raster scanning method. Operation of the particle beam irradiation apparatus will be described hereinafter. The outline of the raster scanning method is described first with reference to FIGS. 1 and 2. FIG. 2 illustrates how an irradiation position A, an irradiation position B, and an irradiation position C shown in FIG. 1 are irradiated sequentially. In FIG. 2, the horizontal axis represents time and the vertical axis represents irradiation positions, and the position of the particle beam 10 scan-shifting with time is indicated by the white arrows. First, the controller 5 controls the Y-direction electromagnet 21 and the X-direction electromagnet 22 of the scanning apparatus 2 for the particle beam to stay at the irradiation position A. When the dose measured with the dose monitor 3 reaches a dose to be imparted to the irradiation position A, i.e., a target dose stored in the storing unit 4, the controller 5 controls the scanning apparatus 2 to scan-shift the particle beam 10 to the irradiation position B. When the particle beam 10 is scan-shifted to the irradiation position B, the controller controls the particle beam to stay there. And then when the dose measured with the dose monitor 3 reaches a target dose to the irradiation position B, the controller controls the scanning apparatus 2 to scan-shift the particle beam 10 to the irradiation position C. While the particle beam 10 is being scan-shifted, i.e., during scanning, the irradiation target (diseased portion) 11 is kept irradiated with the particle beam. For that reason, in order to measure a dose to, for example, the irradiation position B, such a control is performed that the dose measurement is started at the time when the scan-shifting is started from the irradiation position A to the next irradiation position B, and then when the summation of the dose imparted during scan-shifting from the irradiation position A to the irradiation position B and the dose imparted during staying at the irradiation position B reaches a prescribed target dose, scan-shifting is started from the irradiation position B to the next irradiation position C.

Thus, by setting the energy level of the particle beam to a certain value and then performing the irradiation while shifting the particle beam in the two X-Y directions perpendicular to the traveling direction of the particle beam according to the above scanning manner, all irradiation positions in the two-dimensional X-Y plane at a Z-position of a tumor, i.e., a diseased region can be irradiated with the particle beam. In the present invention, all irradiation positions in the two-dimensional X-Y plane at a Z-position are irradiated multiple times with the particle beam with its energy level being kept constant, that is, rescanning is performed.

Figure 3:
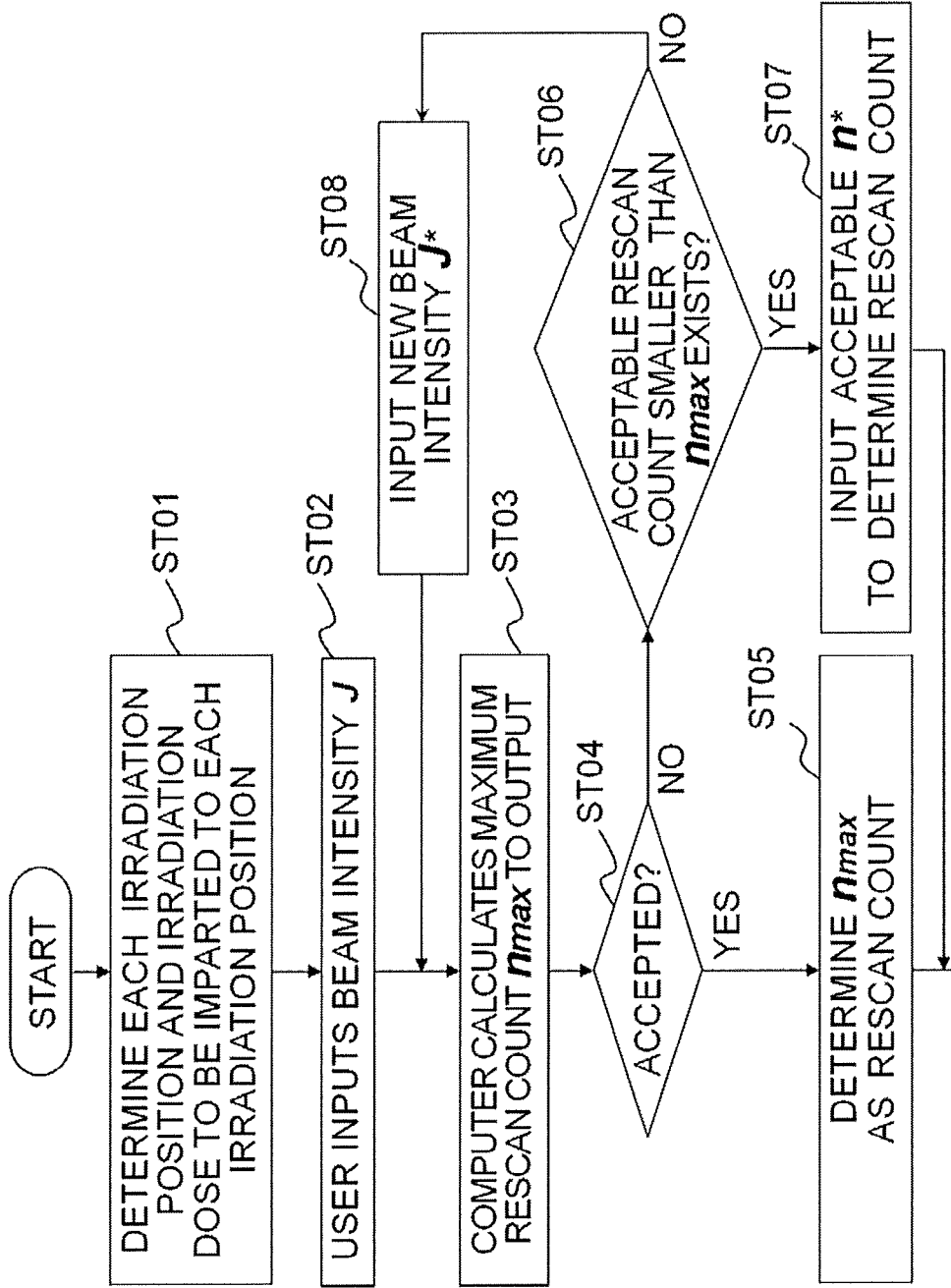
FIG. 3 is a flow diagram showing a calculation procedure of the particle beam irradiation apparatus according to Embodiment 1 of the present invention.

A method of determining the rescan count and the irradiation beam intensity is described below. FIG. 3 is a flow diagram showing a method of determining the rescan count when the beam intensity is fixed in advance. First, each irradiation position i in a tumor and a dose $d_i$ to be imparted to each irradiation position are determined on the basis of CT information of a patient and the position information of the tumor (Step ST01). These positions and the doses are ordinarily determined by a calculation apparatus referred to as "treatment planning apparatus" and stored in the memory 4. Here, the dose $d_i$ to be administered to each irradiation position is defined not as a single dose to be imparted during one scanning divided multiply but as the total of doses to be imparted multiple times to each irradiation position. Accordingly, assuming that the rescan count is n, a single dose to be imparted is expressed as $d_i/n$.

In implementing the present invention, in order to determine a rescan count n, a user of the particle beam irradiation apparatus inputs a beam intensity J to be used for treatment to the calculator 6 via the input/output unit 7 before starting the treatment (Step ST02). The calculator 6 calculates a time $t_i$ required for scan-shifting from an irradiation position i−1 to a next irradiation position, on the basis of the position information on each irradiation position i, the information on a dose $d_i$ to be administered to an irradiation position i, and the information on the scan speed for the scanning apparatus 2 to scan the particle beam. The time $t_i$ can be calculated from, for example, the following equation (1):

$$t_i = \max[(x_i - x_{i-1})/V_x, (y_i - y_{i-1})/V_y] \quad (1).$$

Here, $x_i$, $x_{i-1}$ and $y_i$, $y_{i-1}$ represent the X- and Y-coordinates of the irradiation positions i, and i−1 respectively; and $V_x$ and $V_y$ represent scan speeds in the X- and Y-directions, respectively, by the scanning apparatus. And the max[a, b] is an operator that selects a larger one among a and b. Note that the equation (1) could be a different equation depending on the characteristics of the scanning apparatus 2 and the controller 5.

In order to avoid an excessive dose, a single dose to be administered to each irradiation position must be larger than an actual dose to be imparted during scan-shifting. That is, the following conditional expression (P1) must hold true for all irradiation positions is, except for an irradiation position i to be irradiated first among irradiation positions corresponding to an energy level.

$$J^* t_i \leq d_i / n \quad (P1)$$

Here, J is a beam intensity input as a dose to be imparted per unit time.

Modification of the conditional expression (P1) leads to the following expression (2):

$$n \leq d_i / (J^* t_i) \quad (2).$$

Defining as "$n_{max}$" a maximum rescan count n satisfying the expression (2) for an i that minimizes the right hand of the expression (2) among all i's, the $n_{max}$ is a maximum integer that satisfies the conditional expression (P1) for all i's. Specifically, the $n_{max}$ is expressed below:

$$n_{max} = \text{int}[\min(i)[d_i / (J^* t_i)]] \quad (3),$$

where the operator int[r] expresses a maximum integer not exceeding a real number r, and the operator min(i)[f(i)] expresses a minimum value among f(i)'s for all i's.

The calculator 6 outputs the above-calculated $n_{max}$ to the input/output unit 7 to present it to the user (Step ST03). The user sees the value of $n_{max}$ and if accepts it ("YES" in Step ST04), the $n_{max}$ is determined as a rescan count N (Step ST05). Then, information on the determined count is sent to the memory 4 or the controller 5.

The user sees the $n_{max}$ and if decides that a rescan count n* smaller than the $n_{max}$ is sufficient ("YES" in Step ST06), the user may input anew the modified rescan count n*, to determine the n* as the rescan count N (Step ST07). Then, the rescan count information may be sent to the memory 4 or the controller 5. For example, when the rescanning is performed in such a way that all irradiation positions are irradiated in the order of i=1, 2, . . . , M−1, M for the first time scanning and in the order of i=M, M−1, . . . , 2, 1 for the next time scanning and so on, it is conceivable that an even rescan count is more effective for a uniform dose distribution than an odd rescan count. In that case, if the $n_{max}$ is an odd number, $n_{max}$−1 is input as the rescan count n*.

Otherwise, the user sees $n_{max}$ and if decides, for example, that the $n_{max}$ is insufficient for an uniform distribution and a larger rescan count is required ("NO" in Step ST06), the user may input anew a smaller beam intensity J* (Step ST08).

Then, the calculator 6 executes Step ST03 to recalculate an $n_{max}$.

Figure 4:
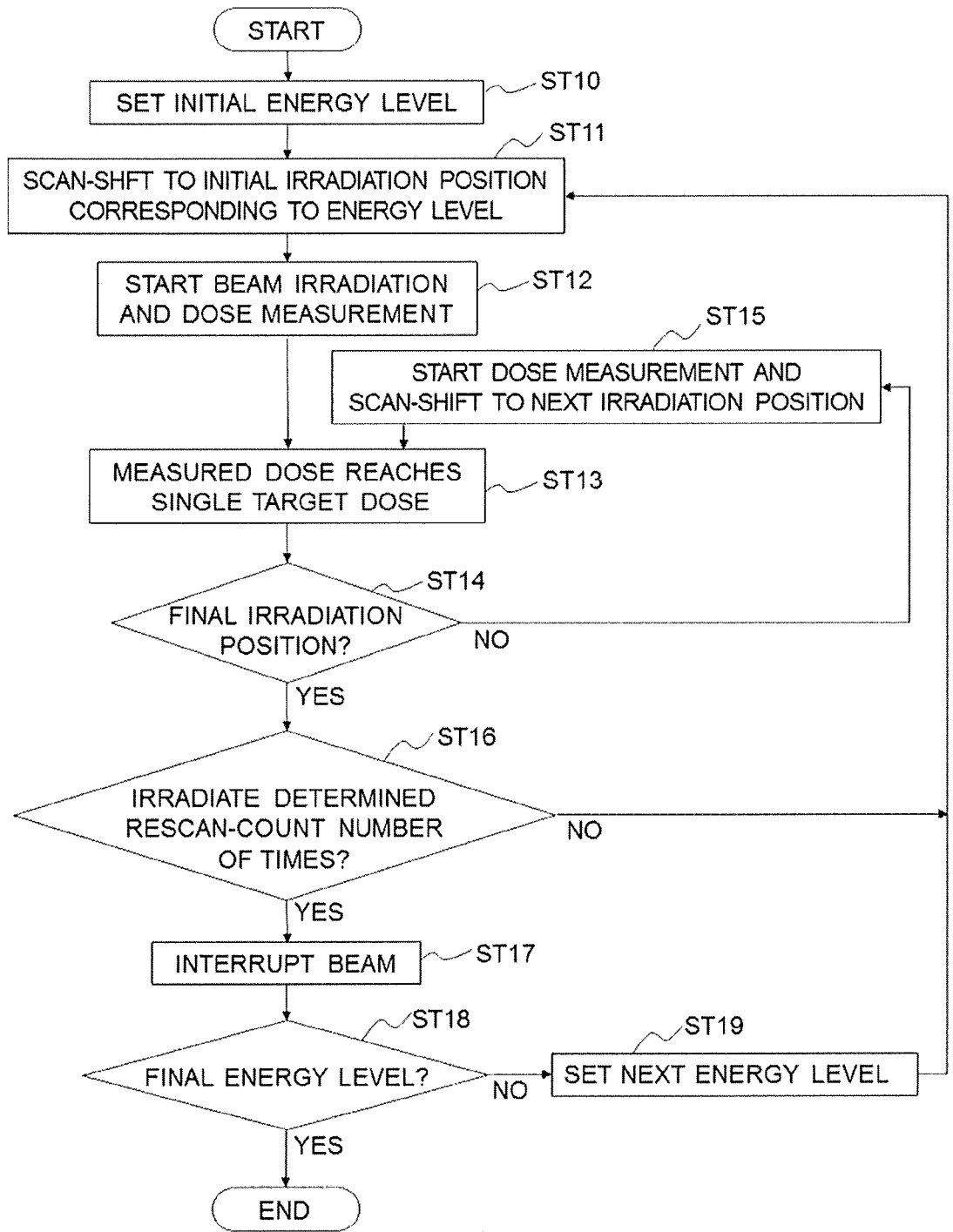
FIG. 4 is a flow diagram showing an irradiation procedure of the particle beam irradiation apparatus according to Embodiment 1 of the present invention.

Using the rescan count N thus determined and the beam intensity J for determining the rescan count N, irradiation is performed in accordance with the flow diagram shown in FIG. 4. First, a parameter of the particle beam generating apparatus 1 is set for the particle beam to have an initial energy level to irradiate (Step ST10). Next, a parameter of the scanning apparatus 2 is set for the particle beam to be located at an initial irradiation position corresponding to the initial energy level (Step ST11). Then, the particle beam is generated to start irradiation, and the dose measurement with the dose monitor 3 is started at the same time (Step ST12).

When a measured dose to an irradiation position reaches a single target dose (Step ST13), determination is made whether or not the irradiation position is the last irradiation position for the beam energy level (Step ST14). If not the last irradiation position ("NO" in Step ST14), the particle beam is scan-shifted to a next irradiation position by controlling the parameter of the scanning apparatus 2. At the same time that the scan-shifting is started from an irradiation position $i_0$ to a next irradiation position $i_1$, the dose monitor 3 starts the dose measurement. When the beam is scan-shifted to the irradiation position $i_1$, the scan-shifting is stopped and the beam stays at the irradiation position $i_1$, with the dose measurement being continued (Step ST15). When the measured dose reaches a dose $d_{i1}/n$ to be imparted during staying at the irradiation position $i_1$ (Step ST13) and if the irradiation position $i_1$ is not the last irradiation position ("NO" in Step ST14), the controller 5 commands start of scan-shifting to a next irradiation position $i_2$ and the dose monitor 3 starts anew the dose measurement at the same time (Step ST15). At that time, the measured dose may be reset in the same measurement mechanism as with the irradiation position $i_1$ before the dose measurement may be started anew. If the reset time causes a problem, two dose monitors 3 may be used one after another to measure a dose to each irradiation position. In either case, the control is performed so that the summation of a dose imparted during scan-shifting from the irradiation position i−1 to the irradiation position i and that imparted during staying at the irradiation position i equals a single dose $d_i/n$ to be imparted to the irradiation position i.

After one irradiation scanning is finished for all irradiation positions corresponding to an energy level, ("YES" in Step ST14), determination is made whether or not the irradiation is performed the determined rescan-count number of times (Step ST16). If the determined rescan-count irradiation are not finished ("NO" in Step ST16), the process returns to Step ST11 to perform the second irradiation, the third irradiation, . . . for each irradiation position corresponding to the same energy level. If all irradiation positions corresponding to the energy level are irradiated the determined rescan-count number of times N ("YES" in Step ST16), the beam is interrupted (Step ST17). Then, determination is made whether or not the energy level is a last one (Step ST18). If the energy level is not the last one ("NO" in Step ST18), the parameter of the particle beam generating apparatus 1 is changed for the particle beam to have a next energy level (Step ST19). The irradiation is repeated in the same way until the energy level is determined to be the last one ("YES" in Step ST18). The single treatment is thus completed.

In the above description, while the total dose $d_i$ to be administered multiple times to each irradiation position is stored in the memory 4 and the measured dose is compares with the single dose $d_i/n$ calculated by the controller 5, the value of $d_i/n$ may be stored in the memory 4 after the maximum rescan count $n_{max}$ is calculated.

As long as the configuration is made such that the calculator 6 acquires the dose $d_i$ to be administered to each irradiation position to calculate the $n_{max}$ from the $d_i$ and finally the controller 5 can acquire the $d_i/n_{max}$, that is, a dose to be administered during one scanning to each irradiation position can be calculated from the total dose to be administered to each irradiation position, any method may be employed for storing and communicating the information on these values.

The calculator 6 and the memory 4 may be made up of other hardware units to have individually the information about the dose to be administered, or may be configured such that only either one has the information to share the information by means of communication when needed. Otherwise, the calculator 6 and the memory 4 may be made up of a one hardware unit.

As described above, according to Embodiment 1 of the present invention, a maximum rescan count is calculated on the basis of an input beam intensity, a scan-shifting time of the particle beam, and a dose to be imparted to each irradiation position, thus providing a particle beam irradiation apparatus that is capable of performing a highly reliable irradiation in a shortest possible time.

Embodiment 2

Figure 5:
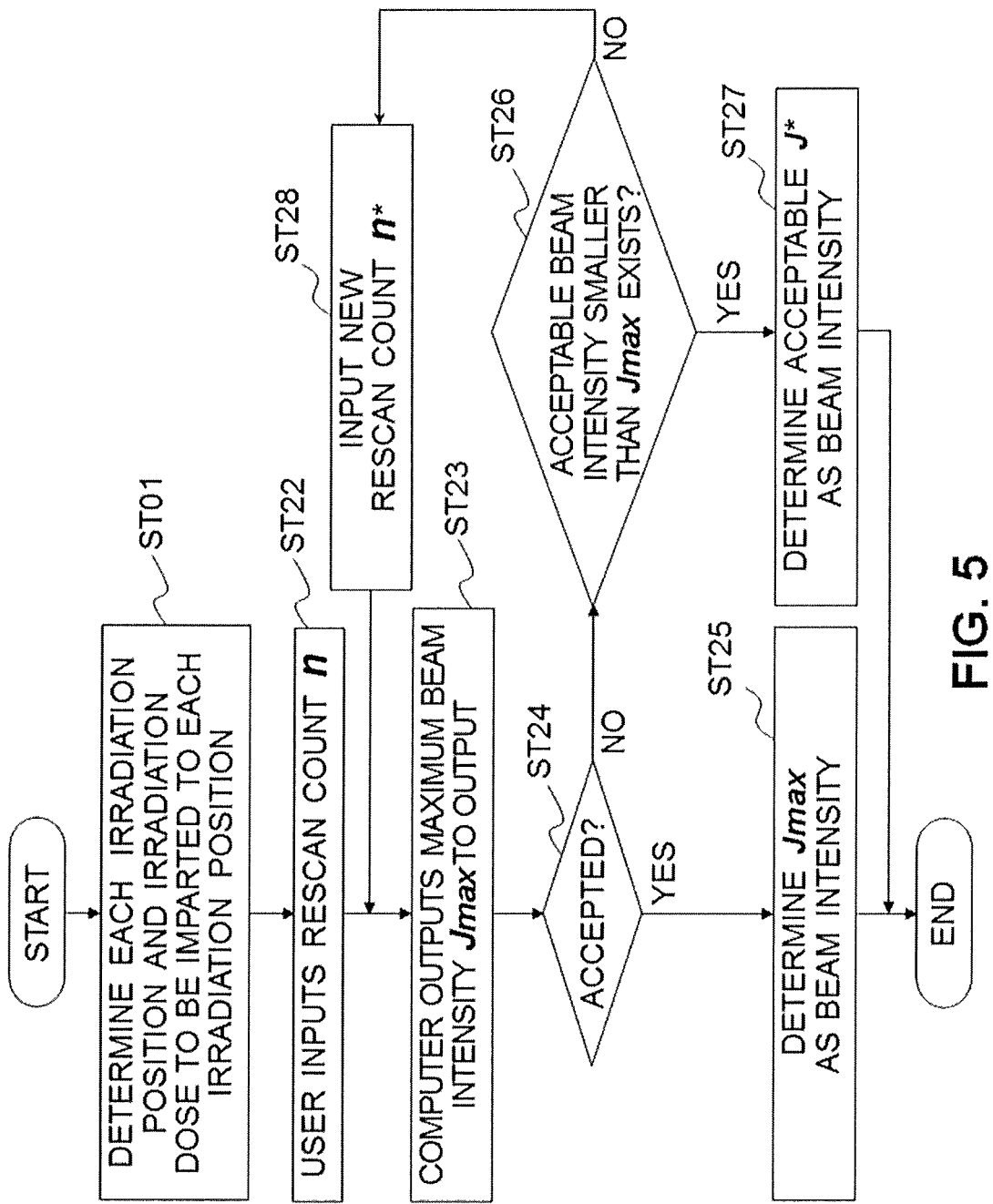
FIG. 5 is a flow diagram showing a calculation procedure of a particle beam irradiation apparatus according to Embodiment 2 of the present invention.

FIG. 5 is a flow diagram showing a calculation procedure of a particle beam irradiation apparatus according to Embodiment 2 of the present invention. The configuration of the apparatus is the same as Embodiment 1. While Embodiment 1 is for implementing the method of determining an optimum rescan count in the case of a beam intensity being predetermined, Embodiment 2 is for implementing a method of determining an optimum beam intensity in the case of a rescan count being predetermined.

The user inputs a predetermined rescan count n to the calculator 6 via the input/output unit 7 (Step ST 22). The calculator outputs a maximum beam intensity that satisfies the conditional expression (P1) for all irradiation positions i (Step ST23). The conditional expression (P1) is transformed into the following expression (4):

$$J \leq d_i/(n^*t_i) \quad (4).$$

Hence, the maximum beam intensity $J_{max}$ satisfying the conditional expression (P1) for all i's is expressed below:

$$J_{max} = \min(i)[d_i/(n^*t_i)] \quad (5).$$

If the beam intensity extracted from the particle beam generating apparatus 1 can be arbitrarily set as continuous values, which depends on the specification of the particle beam generating apparatus 1, the calculator 6 outputs directly the maximum particle beam intensity $J_{max}$ calculated from the above equation (5). However, if the beam intensity extractable from the particle beam generating apparatus 1 is limited to discrete values, the calculator 6 needs to output as a $J_{max}$ a maximum beam intensity that satisfies the equation (5) among settable beam intensities.

If the user accepts the output value of $J_{max}$ ("YES" in Step ST24), the $J_{max}$ is determined as a beam intensity (Step ST25). The procedure for determining beam intensity is now completed, and then the irradiation is started. If the user does not accept the output value of $J_{max}$ ("NO" in Step ST24) and decides that a beam intensity lower than the $J_{max}$ is sufficient ("YES" in Step ST26), the user may determine an acceptable beam intensity J* as an irradiation beam intensity to input it to the calculator 6 (Step ST27).

Otherwise, the user sees the output value of $J_{max}$ and if decides that the $J_{max}$ is insufficient and a large beam intensity is needed ("NO" in Step ST26), the user can input anew a smaller rescan count n* (Step ST28) for the calculator 6 to recalculate a $J_{max}$.

As described above, according to Embodiment 2 of the present invention, a maximum beam intensity is calculated on the basis of an input rescan count, a scan-shifting time of the particle beam, and a dose to be imparted to each irradiation position, thus providing a particle beam irradiation apparatus that is capable of performing a highly reliable irradiation in a shortest possible time.

Embodiment 3

Depending on the specification of a particle beam generation unit, the beam intensity is not always constant. For example, in a case of the particle beam generating apparatus 1 being a synchrotron particle accelerator, it is known that amplitude of the beam intensity fluctuates randomly to some extent with time. Accordingly, a dose possibly varies with time during scanning. For that reason, it is difficult to precisely predict in advance what irradiation position is irradiated at a certain time.

Hence, in Embodiment 1, a method of determining a maximum rescan count $n_{max}$ is conceivable in which a margin is set in advance on the basis of the beam intensity fluctuation so that a single dose during scanning does not exceed that to be imparted even if a beam intensity during scanning is higher than the average beam intensity.

Specifically, the user inputs an average beam intensity $J_{ave}$ and a margin "margin" to determine a maximum rescan count that satisfies the following conditional expression (P1m), instead of the conditional expression (P1), for all irradiation positions i.

$$\text{margin}^* J^* t_i \leq d_i/n \quad (P1m)$$

That is, the calculator 6 calculates the maximum rescan count from the following equation (6) to output.

$$n_{max} = \text{int}[\min(i)[d_i/(\text{margin}^* J_{ave}^* t_i)]] \quad (6)$$

Figure 6:
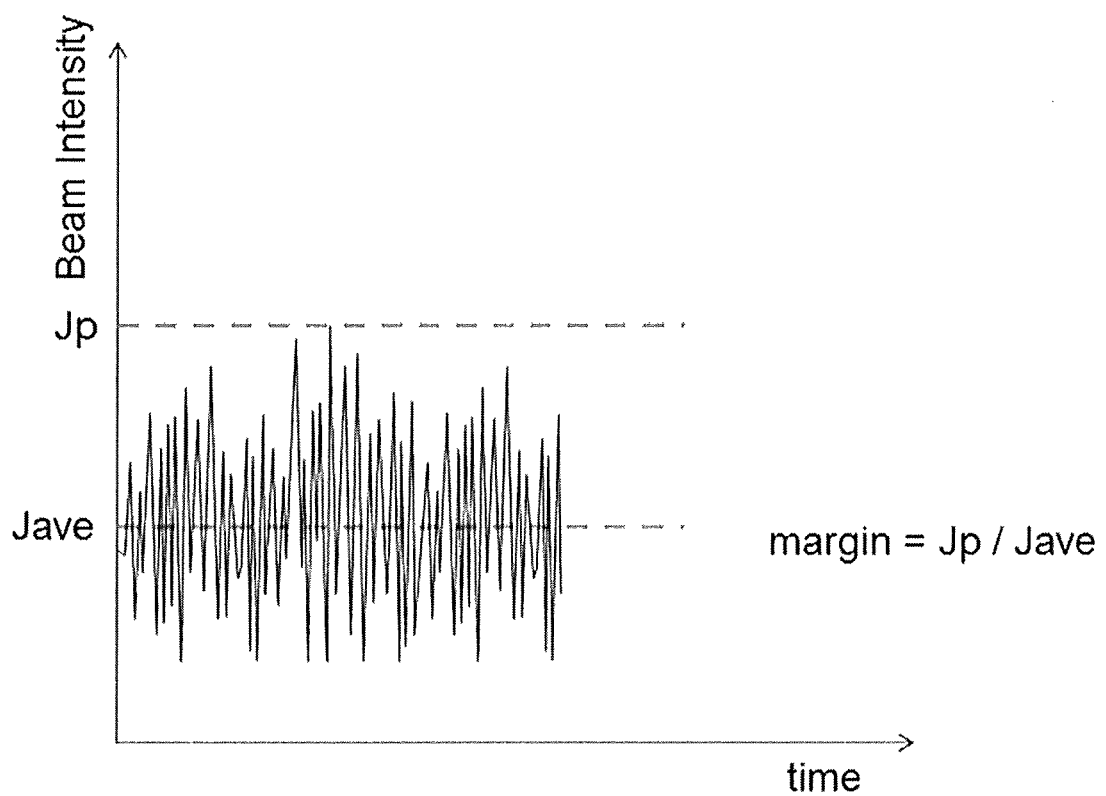
FIG. 6 is a graph for explaining an operation of the particle beam irradiation apparatus according to Embodiment 3 of the present invention.

The value of "margin" should be properly determined depending on the specification of the particle beam generation unit. For example, in a case of a beam intensity being predicted to fluctuate as shown by the solid line in FIG. 6, the "margin" is defined as the ratio of the maximum peak beam intensity $J_p$ to the average value of $J_{ave}$.

Likewise, also in Embodiment 2, considering that the beam intensity fluctuates with time, a margin is set in advance on the basis of the beam intensity fluctuation, and then the calculator calculates from the following equation (7) a maximum average beam intensity $J_{ave,max}$ that satisfies the conditional expression (P1), to output.

$$J_{ave,max} = \min(i)[d_i/(n^* t_i^* \text{margin})] \quad (7).$$

As described above, according to Embodiment 3, a margin is set on the basis of fluctuations of the beam intensity to calculate a maximum rescan count or a maximum beam intensity, thus providing a particle beam irradiation apparatus that is capable of performing a highly reliable irradiation in a shortest possible time even when a particle beam generating apparatus is used that emits a beam whose intensity fluctuates.

Embodiment 4

Figure 7:
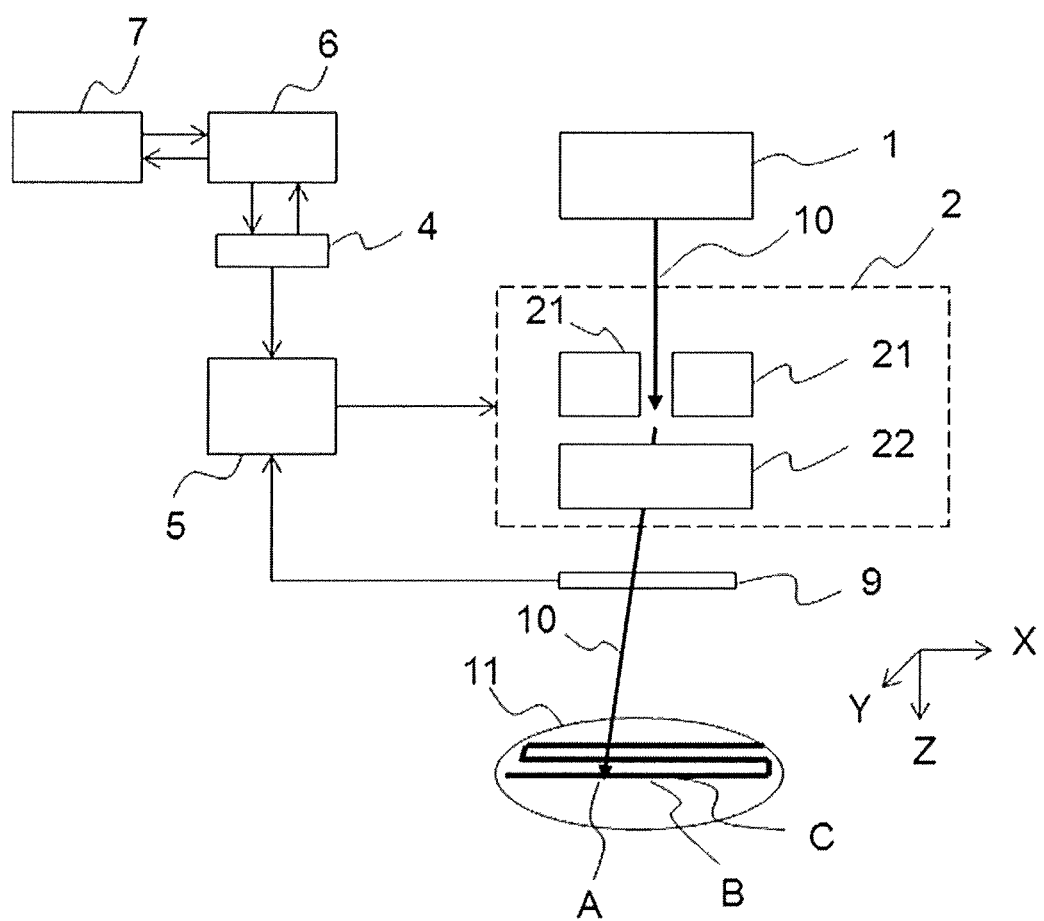
FIG. 7 is a block diagram showing a schematic configuration of a particle beam irradiation apparatus according to Embodiment 4 of the present invention.

FIG. 7 is a block diagram showing a schematic configuration of a particle beam irradiation apparatus according to Embodiment 4 of the present invention. The particle beam irradiation apparatus according to Embodiment 4 includes a particle beam generating apparatus 1 for generating and accelerating particles as a particle beam 10 to a required energy level; and a scanning apparatus 2 for scanning the particle beam 10 generated by the particle beam generating apparatus 1 over given positions in an irradiation target 11, i.e., a tumor of a patient. The particle beam irradiation apparatus further includes a beam position monitor 9 for monitoring the position of the particle beam 10 scanned by the scanning apparatus 2; a memory 4 for storing position information on each irradiation position, information on a dose to be administered to each irradiation position, information on scan speed of the scanning apparatus 2, and the like; a controller 5 for controlling the scanning of the scanning apparatus 2, and a calculator 6 for calculating using the information stored in the memory 4 a rescan count or a beam intensity from a beam intensity or a rescan count input via an input/output unit 7. In addition, the position information to be stored in the memory 4 includes, for example, irradiation position numbers, the X- and Y-coordinates of each irradiation position, current values for energizing the scanning electromagnets in the scanning apparatus 2 to deflect the particle beam to each irradiation position in the X-Y direction, an energy level corresponding to the Z-coordinate of each irradiation position, and the like.

Figure 8:
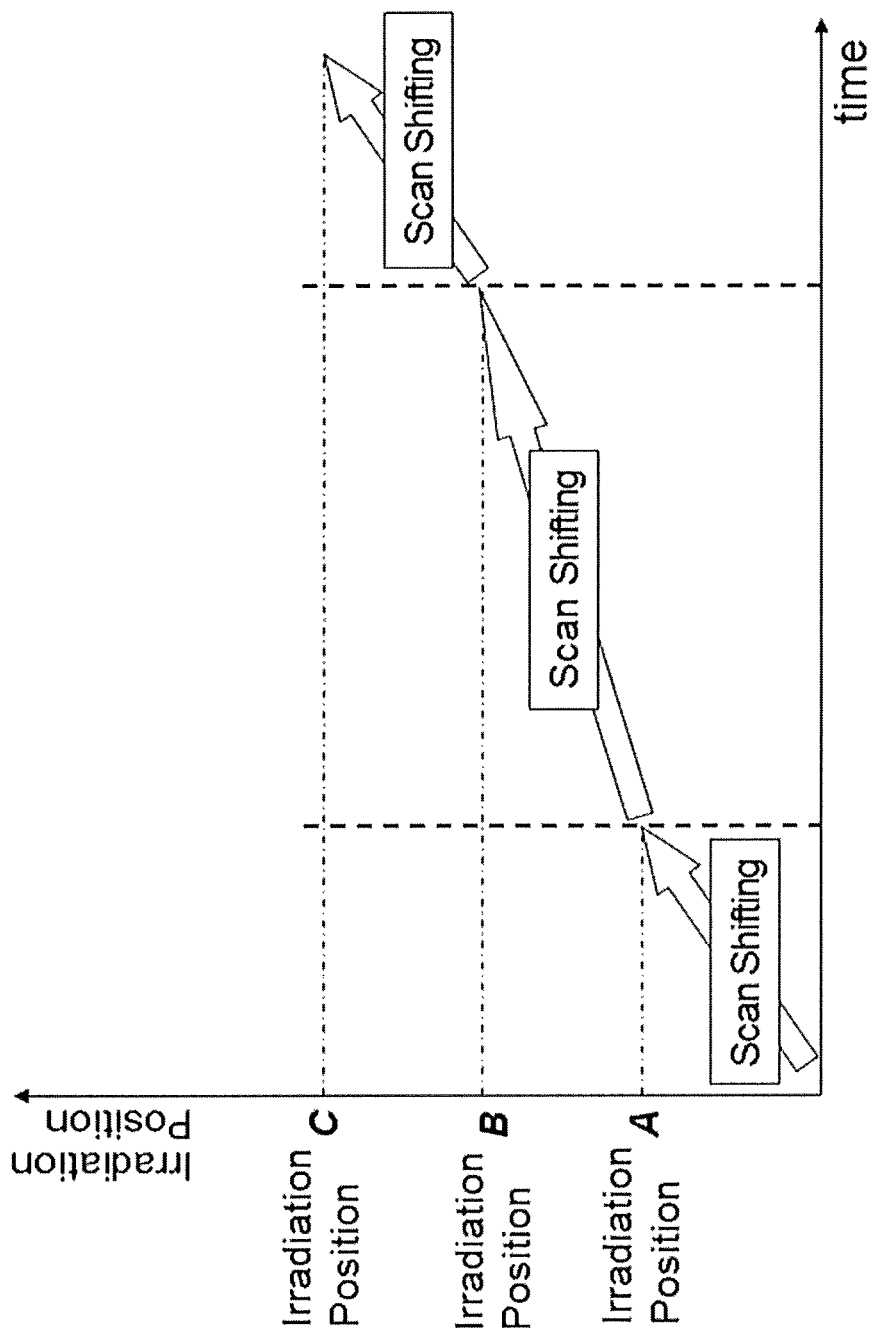
FIG. 8 is a diagram for explaining a basic operation of the particle beam irradiation apparatus according to Embodiment 4 of the present invention.

Embodiment 4 is for a line scanning method. In the line scanning method, the irradiation is performed while continuing scanning of the particle beam without stopping scan-shifting at each irradiation position. A prescribed dose is administered to each irradiation position by scanning the particle beam at a low speed for an irradiation position to which a high dose is to be imparted and at a high speed for an irradiation position to which a low dose is to be imparted, with the beam intensity, which is a dose imparted per unit time, being kept constant. FIG. 8 illustrates how the irradiation is performed by the line scanning irradiation method. In FIG. 8, the horizontal axis represents time and the vertical axis represents irradiation positions, and the position of the particle beam 10 scan-shifting with time is indicated by the white arrows. It is assumed here that the distance from an irradiation position A to an irradiation position B and that from the irradiation position B to an irradiation position C are the same. In FIG. 8, the time of scan-shifting from the irradiation position B to the irradiation position C is shorter than that of scan-shifting from the irradiation position A to the irradiation position B, i.e., the speed of scan-shifting from the irradiation position B to the irradiation position C is faster. As a result, the dose imparted during scan-shifting from the irradiation position B to the irradiation position C is lower than that imparted during scan-shifting from the irradiation position A to the irradiation position B. In this way, in the line scanning method for continuous irradiation with the particle beam, a prescribed dose is administered to each irradiation position, with a dose imparted to each irradiation position being varied by changing the scan-shifting speed depending on an irradiation position.

In rescanning by the above line scanning method, the beam intensity and the rescan count are determines as described below. First, $t_{i,min}$ is defined as a time taken to scan-shift from a given irradiation position i to a next irradiation position i+1 at a maximum speed. The $t_{i,min}$ can be calculated from, for example, the following equation:

$$t_{i,min} = \max[(x_{i+1}-x_i)/V_{x,max}, (y_{i+1}-y_i)/V_{y,max}] \quad (8)$$

where $x_i$, $x_{i+1}$ and $y_i$, $y_{i+1}$ represent X- and Y-coordinates of irradiation positions i, and i+1, respectively; and $V_{x,max}$ and $V_{y,max}$ represent maximum scan speeds in the X- and Y-directions, respectively, by the scanning apparatus.

Then, the following conditional expression (P2) is defined using the $t_{i,min}$ calculated.

$$J*t_{i,min} \leq d_i/n \quad (P2)$$

When the conditional expression (P2) is satisfied for all irradiation positions i, a lower limit of a dose impartable to each irradiation position is lower than a single dose to be imparted thereto, thus allowing a target dose distribution to be formed, without causing an excessive dose, by adjusting properly the scanning speed.

The user inputs a beam intensity J to the calculator 6 and then the calculator 6 calculates a maximum rescan count $n_{max}$ from the following equation (9) to output.

$$n_{max} = \text{int}[\min(i)[d_i/(J*t_{i,min})]] \quad (9)$$

The calculation steps after the user accepts or does not accept the calculated maximum rescan count is exactly the same as with Embodiment 1, i.e., the same as Steps ST04 through ST08 shown in FIG. 3.

Also in the line scanning method, the user may input a rescan count for the calculator 6 to calculate an optimum beam intensity, as with the raster scanning method described in Embodiment 2.

Specifically, the calculator 6 calculates, from the following equation (10) using the rescan count n input by the user, a maximum beam intensity $J_{max}$ that satisfies the conditional expression (P2) for all i's, to present the calculated value to the user.

$$J_{max} = \min(i)[d_i/(n*t_{i,min})] \quad (10)$$

The calculation steps after the user accepts or does not accept the presented value of $J_{max}$ is the same as with Embodiment 2.

As described above, in the line scanning method according to Embodiment 4, either one of a beam intensity J and a rescan count n is input to present a maximum value of the other that satisfies the conditional expression (P2), thus providing a particle beam irradiation apparatus that is capable of performing a highly reliable irradiation in a shortest possible time.

Embodiment 5

In the embodiments so far, it is described that the rescan count n is constant for each energy level of the particle beam, i.e., for each Z-direction position, for the sake of simplicity. However, the rescan count may, as a matter of course, be different for each energy level. It is known that a dose to be imparted to an irradiation position corresponding to a higher energy level is likely to increase in general. Accordingly, the higher the energy level is, the larger number of times an irradiation position corresponding to the energy level can be rescanned to form a uniform dose distribution.

Moreover, the beam intensity is not necessarily constant for all energy levels. For the above reason, increasing the beam intensity for a higher energy level may in some cases be advantageous in shortening the irradiation time. On the other hand, the beam intensity might be essentially difficult to be kept constant for different energy levels, depending on the specification of a particle beam generating apparatus.

A method of determining a rescan count for each energy level is described taking as an example the raster scanning method of Embodiment 1. In order to avoid an excessive dose in the case of a rescan count $n_e$ or a beam intensity $J_e$ being set for an energy level e, a single dose to be administered to each irradiation position must be higher than an actual dose to be imparted during scan-shifting. Hence, a maximum rescan count $n_{e,max}$ that satisfies the conditional expression (P1) for each energy level only needs to be calculated. The conditional expression (P1) for each energy level is expressed below:

$$J_e * t_i \leq d_i / n_e \tag{P1}$$

In a case of beam intensities $J_e$ being given in advance for respective energy levels as with Embodiment 1, the calculator 6 outputs for the respective energy levels all rescan counts $n_{e,max}$ calculated from the following equation:

$$n_{e,max} = \text{int}[\min(i \in e)[d_i/(J_e * t_i)]] \tag{11}$$

where the operator $\min(i \in e)[f(i)]$ represents a minimum value among $f(i)$'s at all irradiation positions i corresponding to a certain energy level.

If the user accepts all these values of $n_{e,max}$'s ("YES" in Step ST04 shown in FIG. 3), these values are determined as rescan counts for respective energy levels. The procedure for determining the rescan counts is now completed. If the user decides that values of $n_e$*s smaller than part or all of the $n_{e,max}$'s are sufficient ("YES" in Step ST06), the user inputs the values of $n_e$*s for the respective rescan counts desired to be modified (Step ST07). Alternative, if the user decides that larger rescan counts are necessary for part or all of the $n_{e,max}$'s ("NO" in Step ST06), the user inputs anew beam intensities $J_e$* lower than the initial beam intensities $J_e$ for rescan counts desired to be modified for respective corresponding energy levels (Step ST08). Then, the computer recalculates rescan counts $n_{e,max}$ for the input beam intensities (Step ST03).

Likewise, in a case of rescan counts $n_e$ being given in advance for respective energy levels as with Embodiment 2, the calculator 6 outputs for the respective energy levels all beam intensities $J_{e,max}$ calculated form the following equation:

$$J_{e,max} = \min(i \in e)[d_i/(n_e * t_i)] \tag{12}$$

If the user accepts all these values of $J_{e,max}$'s ("YES" in Step ST24 shown in FIG. 5), these values are determined as beam intensities for the respective energy levels. The procedure for determining the beam intensities is now completed. If the user decides that values of $J_e$*s smaller than part or all of the $J_{e,max}$'s are sufficient ("YES" in Step ST26), the user inputs the values of $J_e$*s for respective beam intensities desired to be modified (Step ST27). Otherwise, if the user decides that higher beam intensities are necessary for part or all of the $J_{e,max}$'s ("NO" in Step ST26), the user inputs anew rescan counts $n_e$* lower than the initial rescan counts $n_e$ for beam intensities desired to be modified for respective corresponding energy levels (Step ST28). Then, the computer recalculates beam intensities $J_{e,max}$ for the input rescan counts (Step ST23).

While the method of determining a rescan count or a beam intensity for each energy level is described in the above Embodiment 1 or 2 for the raster scanning method, it goes without saying that in Embodiment 4 for the line scanning method, rescan counts or beam intensities may be determined for respective energy levels.

REFERENCE NUMERALS

1: particle beam generating apparatus;
2: scanning apparatus;
3: dose monitor;
4: memory;
5: controller;
6: calculator; and
7: input/output unit

What is claimed is:

1. A particle beam irradiation apparatus that includes:
a scanning apparatus deflecting a particle beam in a two X-Y directions perpendicular to a traveling direction of the particle beam, to scan the particle beam two-dimensionally over irradiation positions in an irradiation target to be irradiate with the particle beam;
a memory that stores position information on the irradiation positions, information on a dose to be administered to each irradiation position, and information on scan speed of the scanning apparatus;
a controller that controls the scanning apparatus; and
a dose monitor that measures a dose of the particle beam, wherein the controller controls the scanning apparatus so that each irradiation position in the irradiation target are irradiated with the particle beam a rescan-count number of times by repeating for the rescan-count number of times the irradiation of all irradiation positions in a two-dimensional X-Y plane by repeating scan-shifting of the particle beam to a next irradiation position without interrupting the irradiation with the particle beam after a dose measured with the dose monitor reaches a dose calculated on the basis of the dose to be administered to a current irradiation position, stored in the memory,
the particle beam irradiation apparatus comprising:
a calculator that receives either one of a rescan count n or a beam intensity J that is a dose of the particle beam per unit time, to calculate a maximum value of the other satisfying the following conditional expression (P1) for all irradiation positions to present the maximum value to a user, $$J * t_i \leq d_i / n \tag{P1}$$

where i is an irradiation position number; $t_i$ is a time for the particle beam to be scan-shifted from an irradiation position i−1 to an irradiation position i, calculated from the scan speed information and the position information stored in the memory; and $d_i$ is a dose to be administered to the irradiation position i, stored in the memory.

2. The particle beam irradiation apparatus of claim 1, wherein the calculator receives either one of a rescan count n and a beam intensity J that is a dose of the particle beam per unit time, to calculate a maximum value of the other satisfying the following conditional expression (P1m), instead of the conditional expression (P1), for all irradiation positions to present the maximum value to a user, $$\text{margin} * J * t_i \leq d_i / n \tag{P1m}$$

where a "margin" is a coefficient set on the basis of intensity fluctuations of the particle beam.

3. A particle beam irradiation apparatus that includes:
a scanning apparatus deflecting a particle beam in a two X-Y directions perpendicular to a traveling direction of the particle beam, to scan the particle beam two-dimensionally over irradiation positions in an irradiation target to be irradiate with the particle beam;
a memory that stores position information on the irradiation positions, information on a dose to be administered to each irradiation position, and information on scan speed of the scanning apparatus; and
a controller that controls the scanning apparatus,
wherein the controller controls the scanning apparatus so that each irradiation position in the irradiation target are irradiated with the particle beam a rescan-count number of times by repeating for the rescan-count number of times the irradiation of all irradiation positions in a two-dimensional X-Y plane by repeating scan-shifting of the particle beam from a current irradiation position to a next irradiation position at a speed calculated on the basis of a dose to be administered to each irradiation position, stored in the memory, the particle beam irradiation apparatus comprising:
a calculator that receives either one of a rescan count n or a beam intensity J that is a dose of the particle beam per unit time, to calculate a maximum value of the other satisfying the following conditional expression (P2) for all irradiation positions to present the maximum value to a user, $$J * t_{i,min} \leq d_i/n \quad (P2),$$

where i is an irradiation position number; $t_{i,min}$ is a minimum time for the particle beam to be able to be scan-shifted from an irradiation position i−1 to an irradiation position i, calculated from the scan speed information and the position information stored in the memory; and $d_i$, is a dose to be administered to the irradiation position i, stored in the memory.

\* \* \* \* \*